United States Patent [19]

Berger, deceased et al.

[11] Patent Number: 4,470,975

[45] Date of Patent: Sep. 11, 1984

[54] METHOD AND COMPOSITION FOR THE ELIMINATION OF WATER FROM AN ANIMAL BODY

[75] Inventors: Hillard Berger, deceased, late of Baltimore, Md., by Adrienne Berger, executrix; W. Gordon Walker, Baltimore, Md.

[73] Assignee: The Johns Hopkins University, Baltimore, Md.

[21] Appl. No.: 844,175

[22] Filed: Oct. 21, 1977
(Under 37 CFR 1.47)

[51] Int. Cl.$^3$ ............................................ C07H 31/72
[52] U.S. Cl. ..................... 424/180; 536/4.1; 536/18.5; 536/56; 536/106; 536/112; 536/103; 536/120
[58] Field of Search ................. 424/180; 536/112, 106, 536/56, 103

[56] References Cited

U.S. PATENT DOCUMENTS

| | | | |
|---|---|---|---|
| 3,624,209 | 11/1971 | Granatek et al. | 424/180 |
| 3,627,872 | 12/1971 | Parkinson et al. | 424/180 |
| 3,865,807 | 2/1975 | Narang et al. | 536/112 |
| 3,934,007 | 1/1976 | Gussin et al. | 424/180 |
| 3,962,429 | 6/1976 | Furuno et al. | 424/180 |
| 3,983,232 | 9/1976 | Pekic et al. | 536/112 |
| 4,002,173 | 1/1977 | Manning et al. | 536/112 |
| 4,070,460 | 1/1978 | Gainer, Jr. | 424/180 |
| 4,076,930 | 2/1978 | Ellingboe et al. | 536/112 |

FOREIGN PATENT DOCUMENTS 854715 11/1960 United Kingdom ................ 536/112

*Primary Examiner*—Johnnie R. Brown
*Attorney, Agent, or Firm*—Cushman, Darby & Cushman

[57] ABSTRACT

It has been found that certain insoluble hydrophilic cross-linked polysaccharides are useful pharmaceutical agents in diverting water elimination from the renal route to the gastrointestinal route, and removing excess water from the body by the gastrointestinal route. These properties are of specific therapeutic value in the treatment of edema, water intoxication in chronic renal failure, in reducing the frequency of hemodialysis, and in the treatment of other forms of fluid retention such as congestive heart failure, cirrhosis of the liver, and other disorders associated with refractory swelling. Sephadex-brand insoluble hydrophilic, cross-linked dextrans are preferred in the practice of the invention.

7 Claims, 9 Drawing Figures

METHOD AND COMPOSITION FOR THE ELIMINATION OF WATER FROM AN ANIMAL BODY

BACKGROUND OF THE INVENTION

In certain diseases, particularly in kidney diseases, water retention within an animal body presents serious difficulties. With total failure of the renal system, water build-up in the body, called edema, can lead to an accumulation in the blood of constituents normally eliminated in the urine, producing a severe toxic condition. This toxic condition can lead to death. The conventional treatment for diseases of this nature is periodic hemodialysis, where artificial kidney machines eliminate water and toxins from the body.

The cost of dialysis is exceedingly high and the availability of dialysis machines is not nearly as great as is convenient for both the practitioner and the patient involved. Additionally, the patient undergoing dialysis may suffer from significant physiological and mental discomfort. For these reasons, it is highly desirable to limit the frequency of dialysis to the minimum number of treatments necessary to preserve health.

Dialysis accomplishes two major objectives, viz. it removes both water and toxins from the body. The toxins are, primarily, substances resulting from protein metabolism. By proper control of the diet of the patient, particularly with regard to the amount of protein in the patient's diet, the necessary frequency of dialysis for removal of these toxins can be considerably reduced as compared to the frequency required with an unrestricted diet. However, unless the patient's consumption of water is severely limited, frequent hemodialysis is still necessary for the removal of water.

Restricting the patient's intake of water is generally very difficult, since patterns of water consumption are often deeply ingrained and changing these patterns may result in severe physical and mental discomfort to the patient. Many patients are not able to restrict their water intake to the minimum necessary for substantial reduction in the frequency of required dialysis.

Accordingly, if a method can be provided for removal of water from the body, then frequency of dialysis could be substantially reduced. Dialysis would, however, still be required for the periodic removal of protein derived toxins, but the frequency of dialysis for this purpose would be far less than the frequency normally required for the removal of both water and protein derived toxins.

SUMMARY OF THE INVENTION

The present invention provides a method of treating edema and thereby reducing the patient's need for dialysis treatment.

It is an object of this invention to treat edema with reduced reliance on hemodialysis by decreasing the rate of renal elimination of water.

It is a further object of this invention to treat edema with reduced reliance on hemodialysis by increasing intestinal water loss.

It is a further object of this invention to provide a new treatment for diseases characterized by an abnormal excess accumulation of fluid within the body, such as, congestive heart failure, cirrhosis of the liver, nephrosis, and other renal diseases associated with fluid retention.

It is a further object of this invention to provide a method of removing water from the gastrointestinal tract, reduce gastrointestinal transit time, and decrease caloric intake.

Surprisingly, it has been found that certain insoluble hydrophilic, cross-linked polysaccharides are useful pharmaceutical agents in diverting water elimination from the renal route to the gastrointestinal route, and removing excess water from the body by the gastrointestinal route; these properties being of specific therapeutic value in the treatment of water intoxication in chronic renal failure, in reducing the frequency of hemodialysis, and in the treatment of other forms of fluid retention such as congestive heart failure, cirrhosis of the liver, and other disorders associated with refractory swelling. These pharmacological properties also provide a means of reducing caloric intake, and hence useful in the treatment of conditions such as obesity.

DETAILED DESCRIPTION OF THE INVENTION

Figure 1:
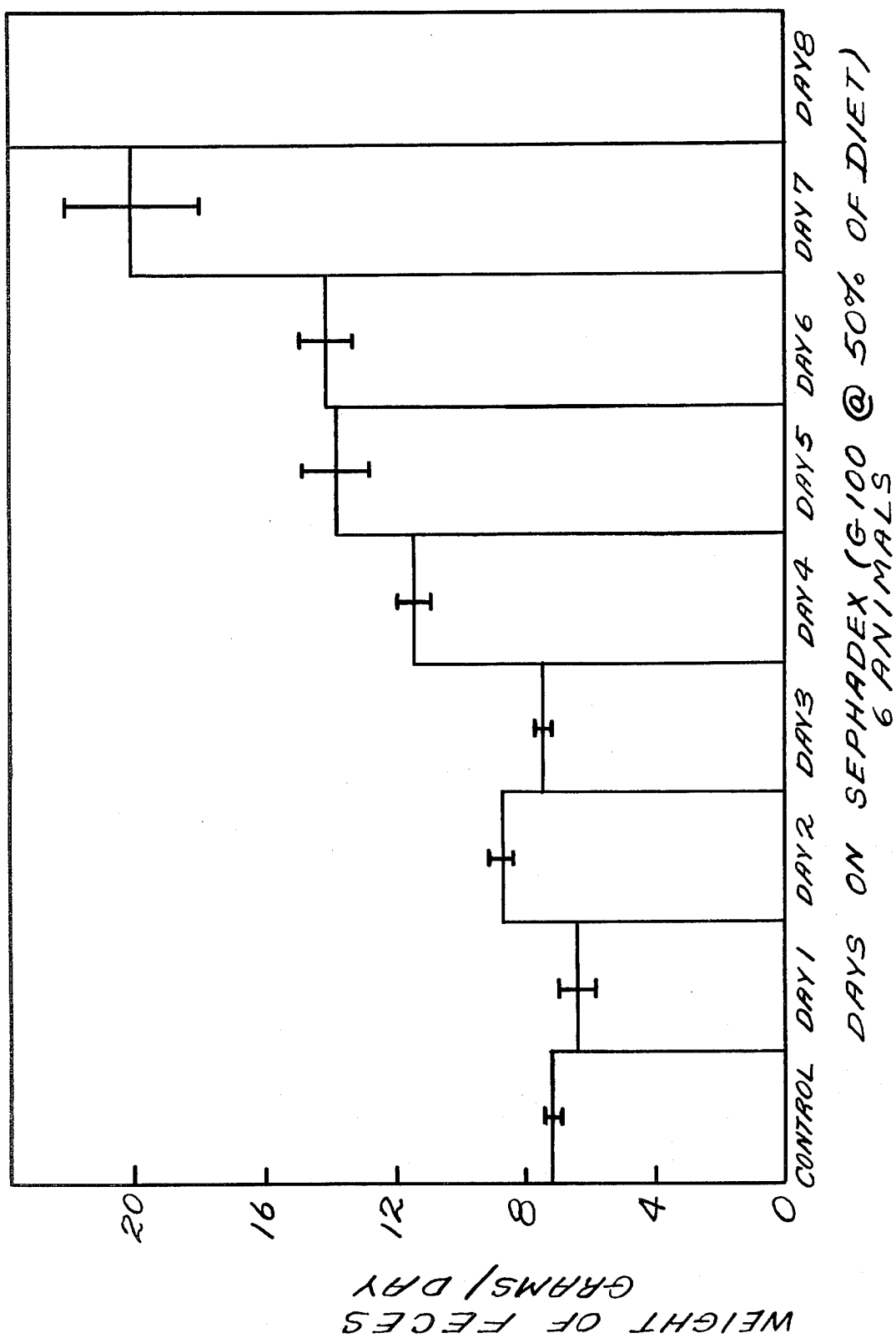
FIG. 1 illustrates the effect of treatment with insoluble, hydrophilic, cross-linked dextrans according to the invention on the weight of feces eliminated by treated rats. It will be noted that the weight of feces of rats treated according to the present invention increases significantly when compared to rats which did not receive treatment.

It has been found in accordance with the present invention that certain insoluble hydrophilic, cross-linked polysaccharides have the ability to bind and keep large quantities of water in the gastrointestinal tract, and hence are useful in the treatment of diseases characterized by an abnormal excess accumulation of fluid within the body. The insoluble hydrophilic, cross-linked polysaccharides of the present invention may be ingested by the patient and during passage of these substances through the digestive system, water passes from the body into the lumen of the gastrointestinal system and is bound by these substances. The bound water is then eliminated by passage from the alimentary canal in the normal manner. As is known, water and urea readily penetrate the lining of the lumen, and by the method of the present invention are continuously bound within the lumen by the insoluble, hydrophilic, cross-linked polysaccharides of the present invention. By binding water and urea in the lumen of the gastrointestinal system with the insoluble, hydrophilic, cross-linked polysaccharides of the present invention, water passing from the body into the gastrointestinal system cannot be taken back into the body, with the result that there is a net decrease in the water content of the body.

As can be appreciated from the foregoing, the insoluble hydrophilic, cross-linked polysaccharides according to the invention must be able to bind water in the gastrointestinal system without being taken up into the body proper through the walls of the intestinal lumen. Further, the insoluble hydrophilic, cross-linked polysaccharides of the present invention must be non-toxic, reasonably palatable, and non-digestible.

The insoluble hydrophilic, cross-linked polysaccharides which are used in the present invention are hydroxyl-group containing non-ionic substances, preferably modified dextrans. In addition to dextrans, other hydroxyl-group containing insoluble hydrophilic cross-linked polysaccharides which are useful in the present invention include modified starch, dextrin, cellulose, and polyglucose, and hydroxyl-group containing uncharged derivatives of these substances or products obtained by a partial depolymerization of the same, as well as fractions thereof.

The dextran or other polysaccharide macromolecules are modified by cross-linking to give a three-dimensional network of polysaccharide chains. Because of their high content of hydroxyl groups, these cross-linked polysaccharides are strongly hydrophilic and swell considerably in water. Various types of insoluble, hydrophilic, cross-linked polysaccharides are available differing in their swelling properties. The degree of swelling is an identifying characteristic of these hydrophilic polysaccharides. The degree of swelling reflects differences in the degree of cross-linkage of the polysaccharides. As is well known in the art, the transport of most organic molecules through the walls of the intestinal lumen requires an active process, and it does not appear that such a process exists for the insoluble hydrophilic, cross-linked polysaccharides of the present invention.

The preparation of the insoluble, hydrophilic, cross-linked polysaccharides used in the present invention is fully described in a series of British and United States patents assigned to Aktiebolaget Pharmacia, a Swedish company. These patents, each of which is hereby incorporated by reference in the present application, are:

| British Patent | U.S. Pat. No. |
| --- | --- |
| — | 3,002,823 |
| 854,715 | 3,042,667 |
| 936,039 | 3,275,576 and 3,277,025 |
| 974,054 | 3,208,994 |
| 1,013,585 | — |

It is to be understood that the disclosures of the above-listed British and United States patents are related, but are not necessarily identical. For example, although Examples 1 to 14 of U.S. Pat. No. 3,042,667 are virtually identical to Examples 4 to 18 of British Pat. No. 854,715, the disclosure and claims of the British patent include both water soluble and water insoluble hydrophilic cross-linked dextrans, whereas the United States patent disclosure is limited to water-insoluble hydrophilic cross-linked dextrans. The hydrophilic, cross-linked polysaccharides used in the present invention are all of the water-insoluble type. The disclosures of the five United States patents listed above, hereby incorporated by reference in the present application, enable one of ordinary skill in the art to prepare the insoluble, hydrophilic, cross-linked polysaccharides useful in the present invention. The four British patents listed above, as well as the disclosures of U.S. Pat Nos. 3,300,474 and 3,542,759, hereby incorporated by reference in the present application, are referred to for additional disclosure of insoluble hydrophilic, cross-linked polysaccharides useful in the present invention.

The preferred insoluble hydrophilic, cross-linked polysaccharides used in the present invention are copolymerization products in the form of gel grains comprising a three-dimensional macroscopic network of dextran substances, built up of chains of mainly alpha-1,6-glucosidically bonded glucose residues, bonded together by ether bridges of the general type —R—O—X—O—R—, wherein R represents the dextran substances and X is an aliphatic radical containing from 3 to 10 carbon atoms, the copolymerization product being water-insoluble but being capable of absorbing water with swelling, the water regain of the product being within the range of about 1 to 50 grams per gram of the dry gel product. The "water regain" of the dry gel product is the amount of water in grams which can be absorbed by one gram of the dry gel. The capacity of swelling of the gelled product may be measured in terms of the water regain. While water regain in the range of about 1 to about 50 grams of water per gram of dry gel product is preferred, dry gel products exhibiting a water regain in the range of about 1 to about 85 grams of water, or even more, are useful in the practice of the present invention. Indeed, it will be understood that the maximum water regain of the product is limited by the ability of the cross-linked polysaccharides used in the present invention to resist degradation in the gastrointestinal system.

In general, the process for preparing the preferred insoluble hydrophilic, cross-linked dextrans used in the present invention can be characterized as a block polymerization process in which a substituted dextran is reacted with a bifunctional organic substance containing halogen and/or epoxy groups, capable of reacting with the hydroxyl groups of the substituted dextran to form ether-linkages. The reaction is conducted in the presence of an alkaline substance which may function either as an acceptor for the hydrohalide liberated as a result of the reaction (when the reaction that forms the basis of the ether-formation is a condensation in which a hydrohalide is split off), or the alkaline substance may act as a catalyst when the reaction is a pure reaction of addition. The block copolymers thus formed are insoluble in water, but capable of swelling therein. Examples of suitable alkaline substances are the alkali metal hydroxides, preferably sodium hydroxide and the alkaline earth metal hydroxides, and also tertiary amines and quaternary ammonium hydroxides.

The block polymerization process takes place in the presence of water and is catalyzed by the alkaline substances described above. As previously stated, all essential details of the preparation of the insoluble hydrophilic, cross-linked dextrans and other polysaccharides used in the present invention are set forth in the five United States patents incorporated by reference herein. Additional details of the preparation of the hydrophilic cross-linked polysaccharides useful in the present invention may be found in four British patents incorporated by reference herein, and in U.S. Pat. Nos. 3,300,474 and 3,542,759 incorporated by reference herein.

The preferred insoluble, hydrophilic, cross-linked dextrans of the present invention are sold by Pharmacia Fine Chemicals, Inc., 800 Centennial Avenue, Piscataway, N.J. 08854 under the trademark Sephadex. Sephadex-brand insoluble, hydrophilic, cross-linked dextrans are available from Pharmacia subsidiaries or representatives in most countries of the world. A list of suppliers may be obtained by writing directly to Pharmacia Fine Chemicals, Inc., Uppsala, Sweden.

EXAMPLE 1

Five normal Sprague-Dawley rats were placed in metabolic cages and urine output on standard rat chow and free access to water measured for a period of five days. During this period, the mean urinary excretion rate in milliliters per day for the entire group was $14.72 \pm 0.95$ (standard error of mean, hereinafter SEM). The animals were subsequently given Sephadex (G-50) mixed with food in equal proportions. They were maintained on this regimen for an additional 7 days. During this latter treatment the mean daily urinary excretion rate was $3.5 \pm 0.48$ (SEM) ml per day, a highly significant difference.

EXAMPLE 2

Six Sprague-Dawley rats were divided into 2 groups of 3 each. One group was given regular or standard rat chow and water ad lib and the second group was given the rat chow ground and mixed with equal parts of Sephadex (G 50) and permitted water ad lib. These studies were carried out for a period of 9 days. During this 9 day period the average daily water intake for the group that received no Sphadex was 30.5 ml per day ($\pm 1.6$ ml SEM). During the same time, they excreted an average daily urine output of $8.54 \pm 0.66$ ml per day. In contrast, the group receiving Sephadex ingested more water, an average daily intake of $46.72 \pm 2.0$ ml per day but put out no measurable quantity of urine. For a subsequent 4 day period, the Sephadex was discontinued and on day 3 and 4 of this last period water intake and urine output for the 2 groups was indistinguishable.

EXAMPLE 3

Figure 2:
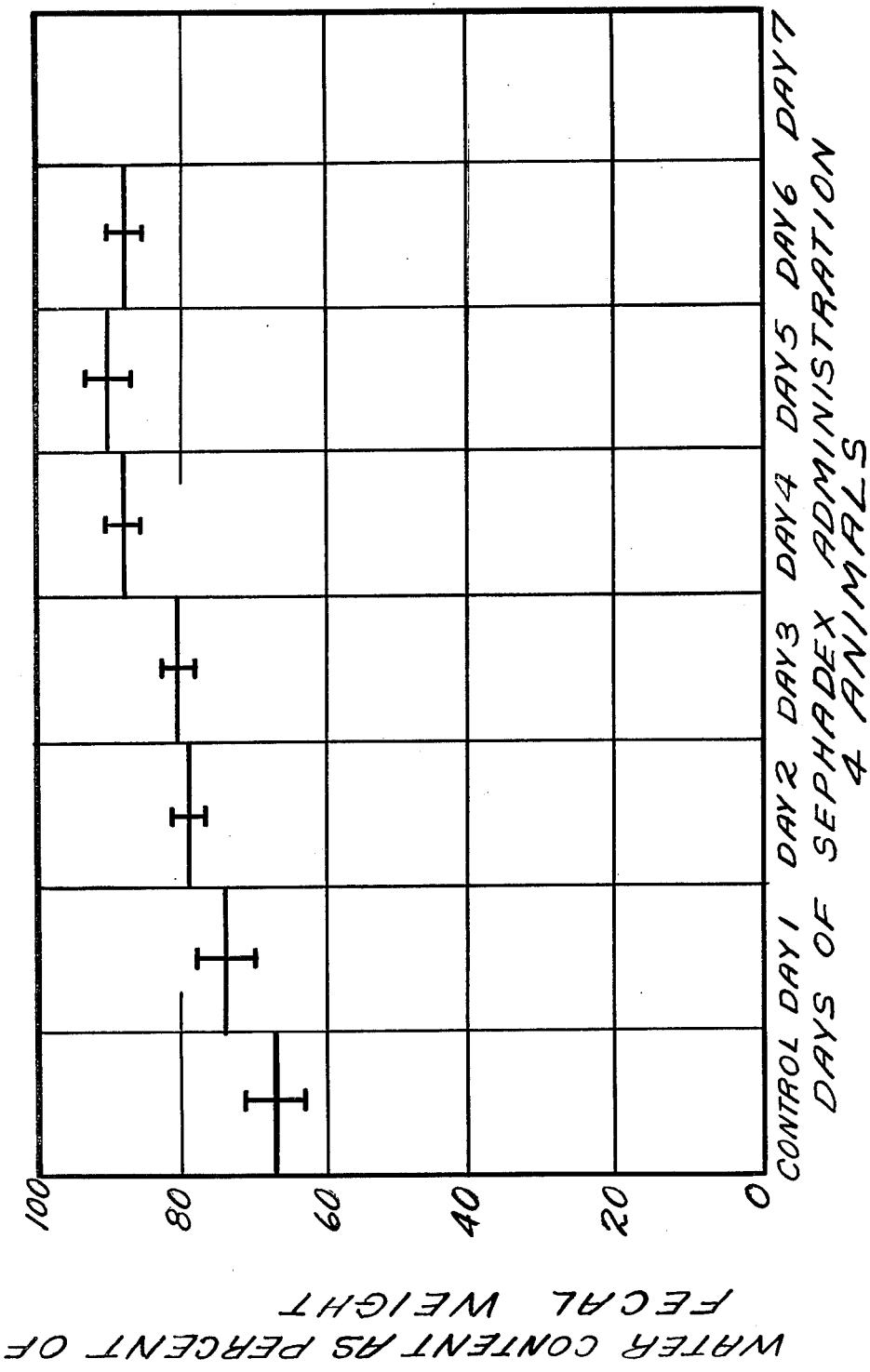
FIG. 2 shows the effect of treatment with insoluble, hydrophilic, cross-linked dextrans according to the invention on water content as a percentage of the weight of feces of rats treated according to the present invention. It will be noted that the water content of feces of rats treated according to the present invention is significantly higher than that of untreated rats.

The quantity of water excreted by way of the feces was measured in 10 animals. Ten male Sprague-Dawley rats were given Sephadex G 100 mixed in 1 to 1 ratio with pulverized purina rat chow. In 6 of the animals the weight of the feces excreted per day was determined. In 4 animals the water content of the feces was measured. The results of the study are shown in FIGS. 1 and 2. Fecal excretion per animal on the control day was 7 grams and the water content 65%. Thus, at the beginning of the study the animals were excreting approximately 4.5 ml of water in the feces. This rose steadily during this study so that by day 7 the animals were excreting 20 grams of feces per day per animal and the water content had risen to 90%. Thus, the fecal water loss after 7 days on the Sephadex regimen was 18 ml per day and increased fecal water loss of more than four-fold. This increased water loss in the feces was even greater than average daily urinary excretion volumes in control animals cited in experiment 2 above. Thus the combination of examples of 1, 2 and 3 demonstrate that the sharp diminution and disappearance of urine production is associated with a comparable increase in water loss from the gastrointestinal tract.

EXAMPLE 4

Rats with non-functioning kidneys.

Figure 3:
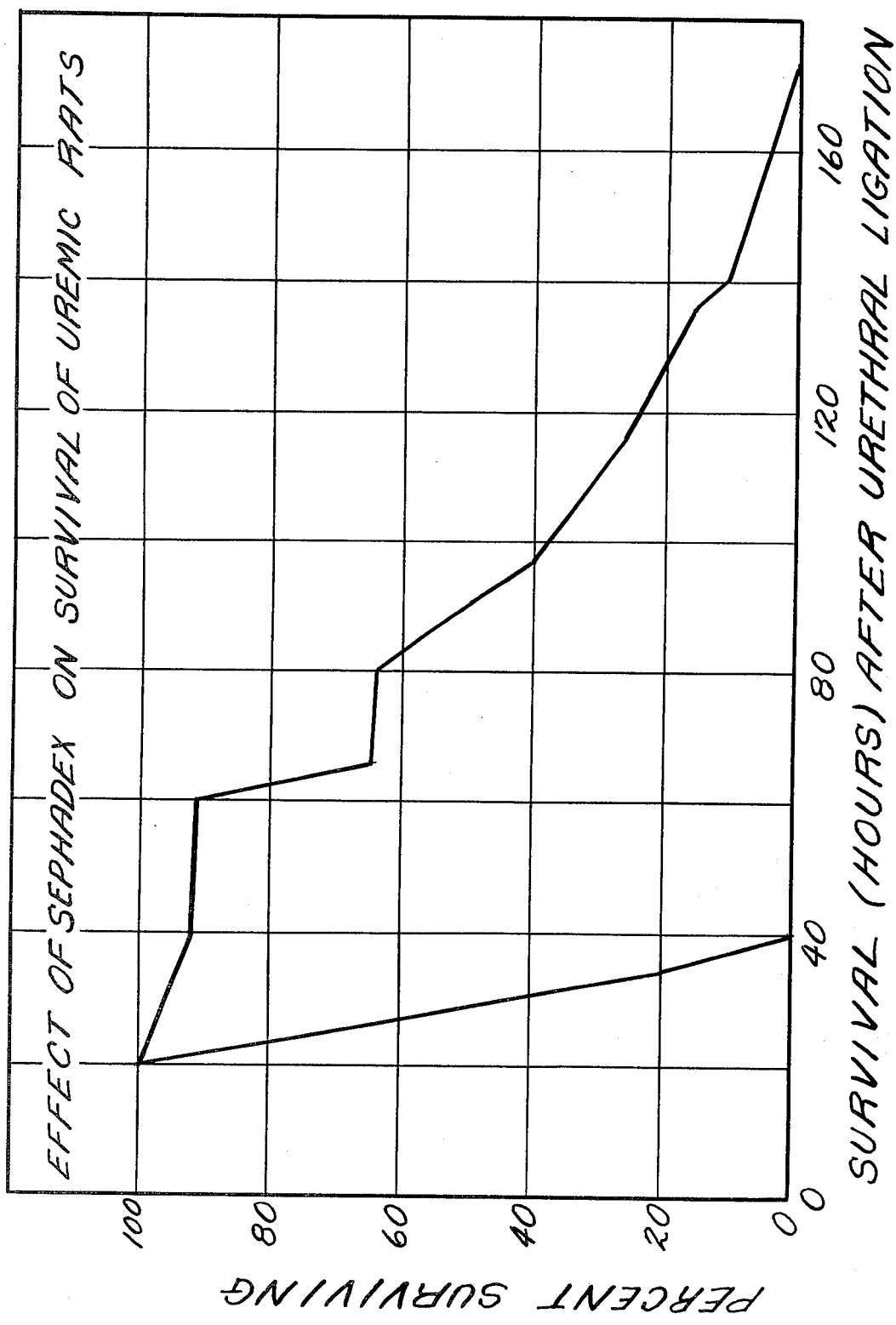
FIG. 3 shows the effect of the use of insoluble, hydrophilic, cross-linked dextrans according to the present invention on the survival of rats with urethral ligation. It will be noted that rats treated with insoluble, hydrophilic, cross-linked dextran according to the present invention survived significantly longer than rats which received no treatment.

Sixteen male Sprague-Dawley rats had their kidney function terminated abruptly by urethral ligation. The rats were then divided into a control group of 4 animals and an experimental group of 12 animals. To ensure that all animals took in a constant quantity of either Sephadex (G50) or a placebo, the Sephadex was suspended in mineral oil and given to the experimental or treatment group. A comparable mixture of mineral oil placebo was given to the control group of animals. The results of the study are shown in FIG. 3. A striking difference in survival time was noted. All control animals were dead in less than 40 hours whereas the experimentally treated group survived for more than 100 hours. (Mean survival time: experimental group $103.25 \pm 10$ hours; survival time for control group $36.25 \pm 1.25$ hours). During the study period, the water intake in these animals did not differ significantly. The control group took in an average of $0.73 \pm 0.11$ ml of water per hour and the group treated with Sephadex (G50) took an average of $0.58 \pm 0.04$ ml of water per hour. Six of the treated animals survived 5 days and one animal survived for 7 days. The treated group received 1.4 grams of Sephadex per day per animal for the duration of their survival. The congrol group received only placeboes of mineral oil. All animals were permitted food and water ad lib for the duration of their survival. Another group of 8 animals operated upon at a different time were submitted to uretheral ligation to serve as controls. All of these animals died between the first and second day.

Thus the addition of Sephadex to the regimen of these rats without any kidney function resulted in an increase in mean survival time of more than three-fold demonstrating that Sephadex exerts an important beneficial effect upon the length of survival in uremia. The information contained in the 3 preceding examples and the present one demonstrates that Sephadex when given orally leads to profound reduction in the rate of urine formation and produces a comparable increase in the quantity of water excreted in the feces. Further, when given to rats rendered uremic by uretheral ligation (thereby preventing any urine excretion) it increases the survival time three-fold. On the basis of this information, it would be expected to behave in the same manner when used in humans without renal function.

EXAMPLE 5

Figure 4:
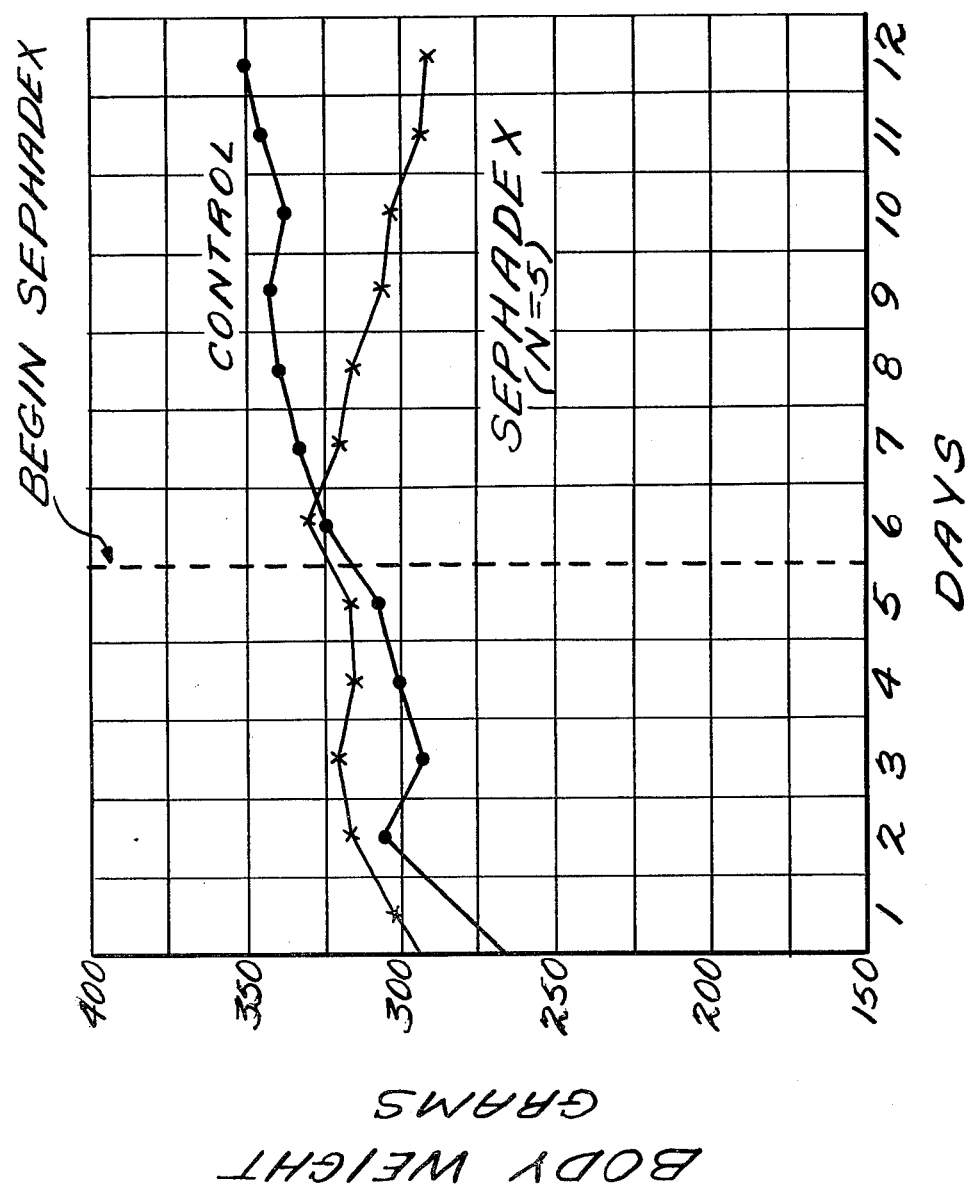
FIGS. 4 and 5 illustrate the effect of administering insoluble, hydrophilic, cross-linked dextran according to the invention on the body weight of rats. It will be noted that shortly after the beginning of treatment the body weight of treated rats began to drop, becoming significantly lower than the body weight of untreated rats.

Six Sprague-Dawley rats were maintained under control conditions in metabolic cages for a 5 day period during which time food intake was weighed carefully while they were permitted food ad lib. They were also permitted free access to water. During this control period, the daily food intake averaged 20.69±0.82 (SEM) grams per day. Beginning on day 6, five of the animals were given food mixed with 50% Sephadex (G 50) and a sixth animal served as a control to document weight changes in an animal not receiving Sephadex during this period. Balance studies were continued throughout this period and daily food intake measured. The results of this study are shown in FIG. 4. The grams of food ingested by the group of animals receiving Sephadex fell to 11.4±0.95 grams per day, a 50% reduction in food intake. During this period of time, the average body weight of the group receiving Sephadex dropped from 330 grams to 290 grams, an average weight loss per animal of 40 grams or more than 10% of the body weight. The lone control animal gained 25 grams during the same period and during that period he continued to ingest an average daily weight of food of 27.1±1.98 grams.

Figure 5:
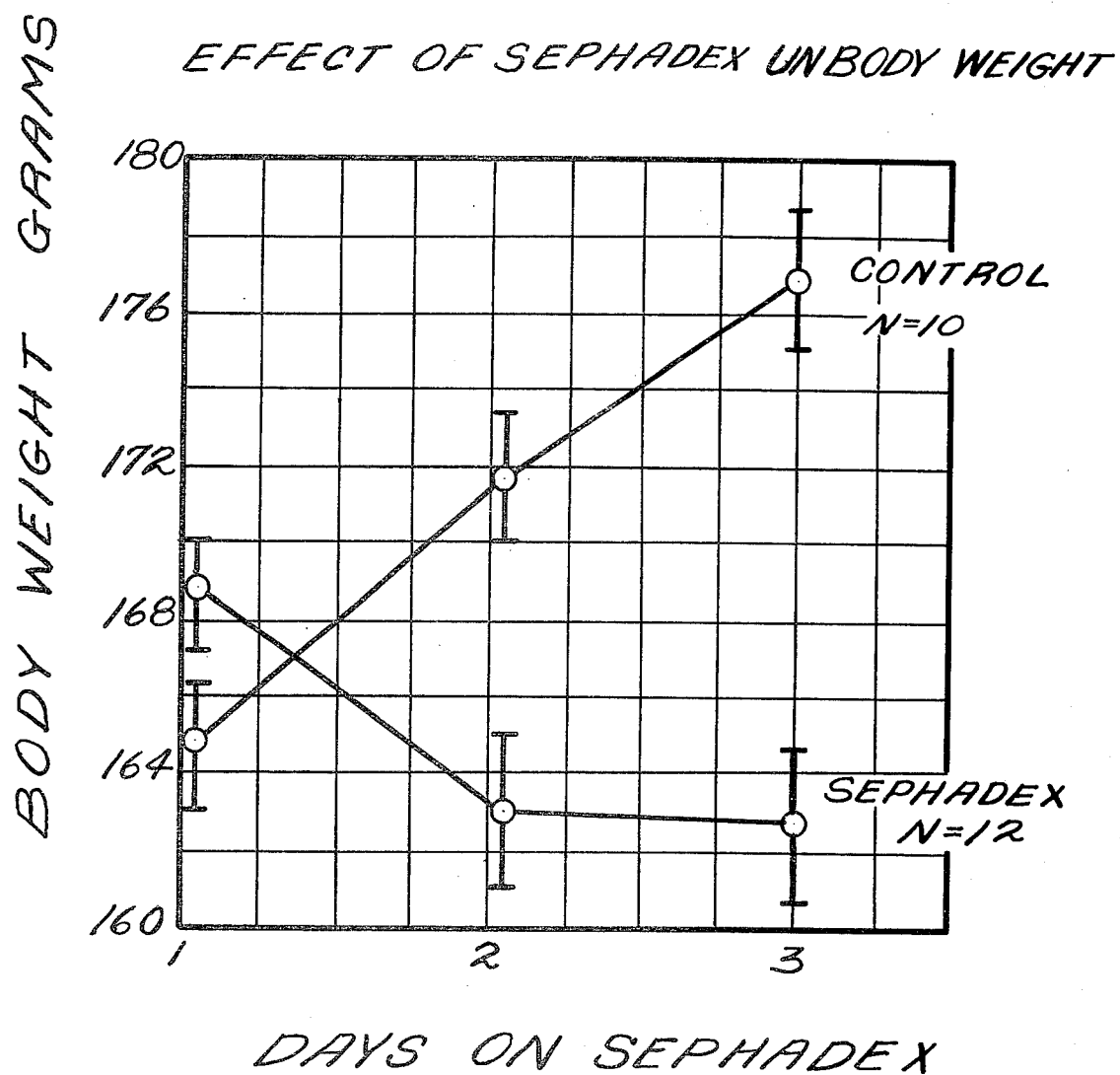

In a second but somewhat shorter experiment a group of 27 animals were divided into a group of 10 control animals and 17 animals receiving Sephadex (G 50). The animals were kept in metabolic cages; the control animals were given Purina rat chow and water ad lib and the Sephadex animals received their food as a 50% mixture of Sephadex (G 50) in pulverized Purina rat chow. During this study the 17 animals receiving Sephadex lost an average of 5 grams of body weight whereas the control group gained an average of 12 grams. The results of this study are shown in FIG. 5. These studies provide evidence that the daily ingestion of Sephadex is associated with the corresponding reduction in caloric or food intake.

EXAMPLE 6

Figure 6A:
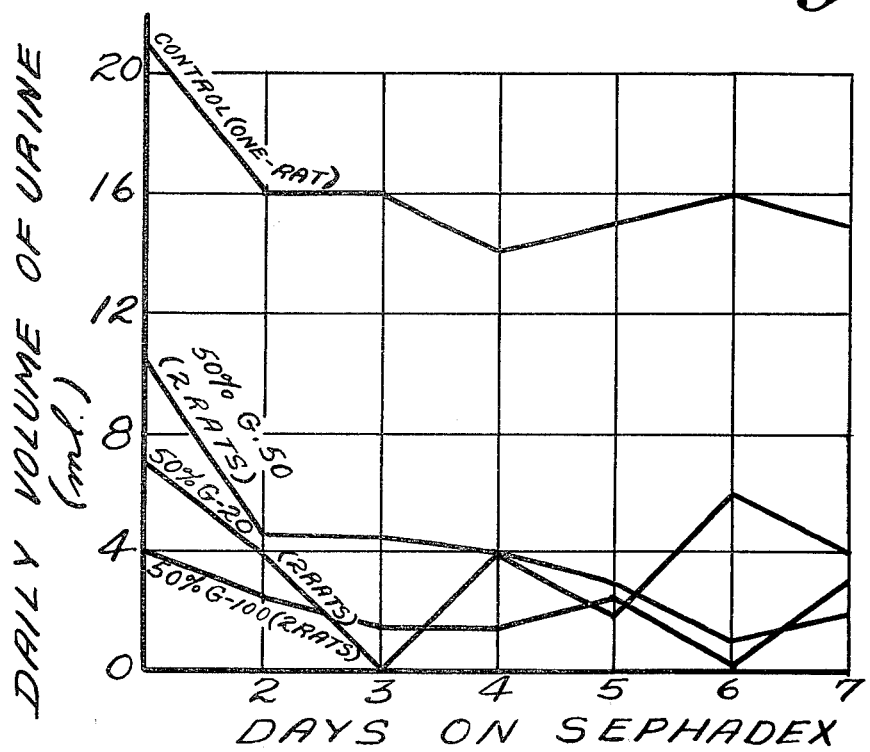
FIGS. 6A and 6B illustrate the effect of treatment on the volume of urine and water content of the feces of rats treated according to the present invention. It will be noted that the volume of urine of rats treated according to the present invention was substantially lower than the volume of untreated rats, and that at the same time, the water content of the feces of treated rats increased compared to the water content of the feces of untreated rats.
Figure 6B:
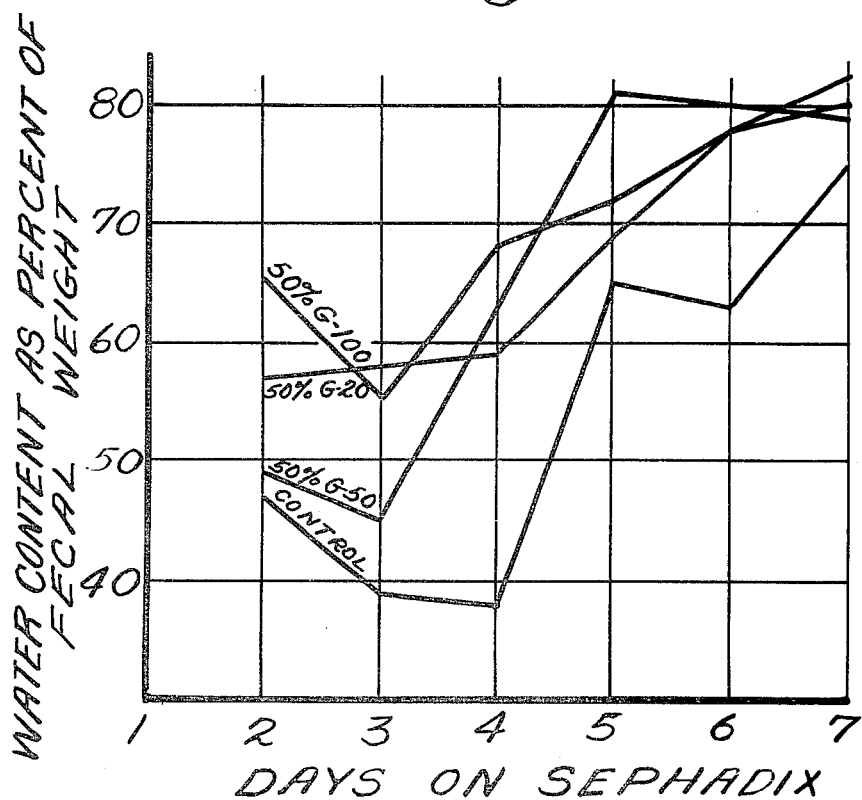

FIG. 6A illustrates an experiment demonstrating the effect of treatment with three different insoluble, hydrophilic, cross-linked dextrans according to the present invention. A group of two rats were given a diet which consisted of 50% by weight Sephadex G-50 and 50% normal rat chow. Another group of 2 rats were given a diet which consisted of 50% by weight Sephadex G-100 and 50% normal rat chow. A third group consisting of a single rat was given a diet which consisted of 50% by weight of Sephadex G-200 and 50% normal rat chow. A control group consisting of a single rat was given a normal diet consisting entirely of normal rat chow. From FIG. 6A, it can be seen that in each case treatment with an insoluble, hydrophilic, cross-linked dextran according to the present invention resulted in a substantially reduced volume of urine, compared to the volume of the control group. At the same time, it can be seen from FIG. 6B that the water content of the feces of rats given a diet containing an insoluble hydrophilic, cross-linked dextran according to the present invention is significantly higher than the water content of the feces of the control group. Both groups were permitted to consume as much water as they desired, and their actual water consumption is shown in the table below:

| | DAILY VOLUME OF WATER CONSUMED (IN MILLILITERS) | | | |
|---|---|---|---|---|
| Day | Control | 50% G-50 | 50% G-100 | 50% G-200 |
| 1 | 52 | 32 | 18 | 41 |
| 2 | 46 | 30 | 43 | 33 |
| 3 | 42 | 24 | 40 | 0 |
| 4 | 30 | 35 | 55 | 52 |
| 5 | 40 | 58 | 48 | 50 |
| 6 | 50 | 65 | 69 | 60 |
| 7 | 50 | 60 | 75 | 50 |

EXAMPLE 7

Figure 7A:
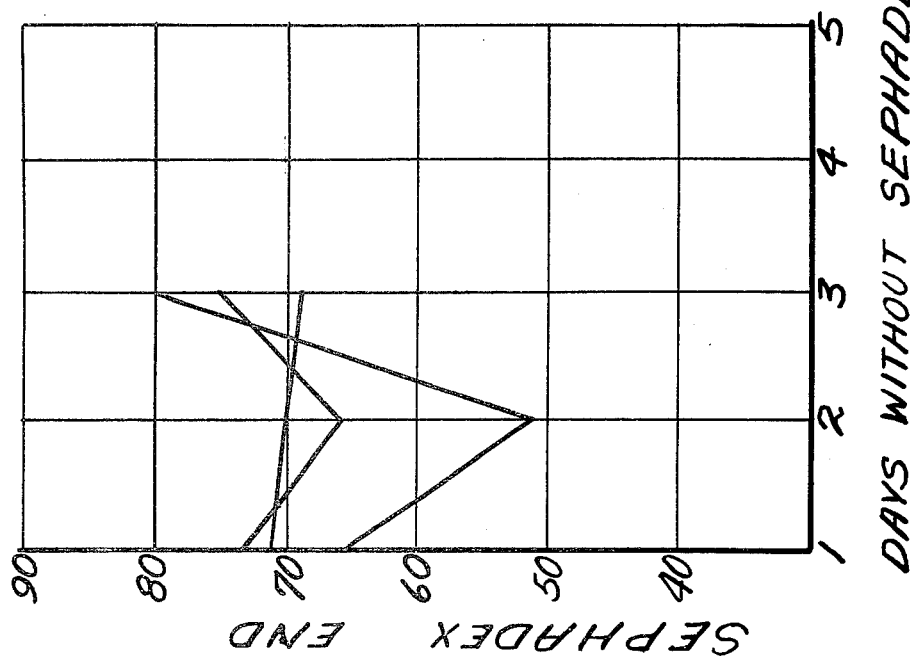
FIGS. 7A and 7B illustrate the effect of treatment of various concentrations of the preferred insoluble, hydrophilic, cross-linked dextrans of the present invention on the volume of urine of treated rats and the water content of the feces of treated rats. After treatment was ended, the volume of urine and water content of the feces of the rats were again measured and are also illustrated.
Figure 7B:
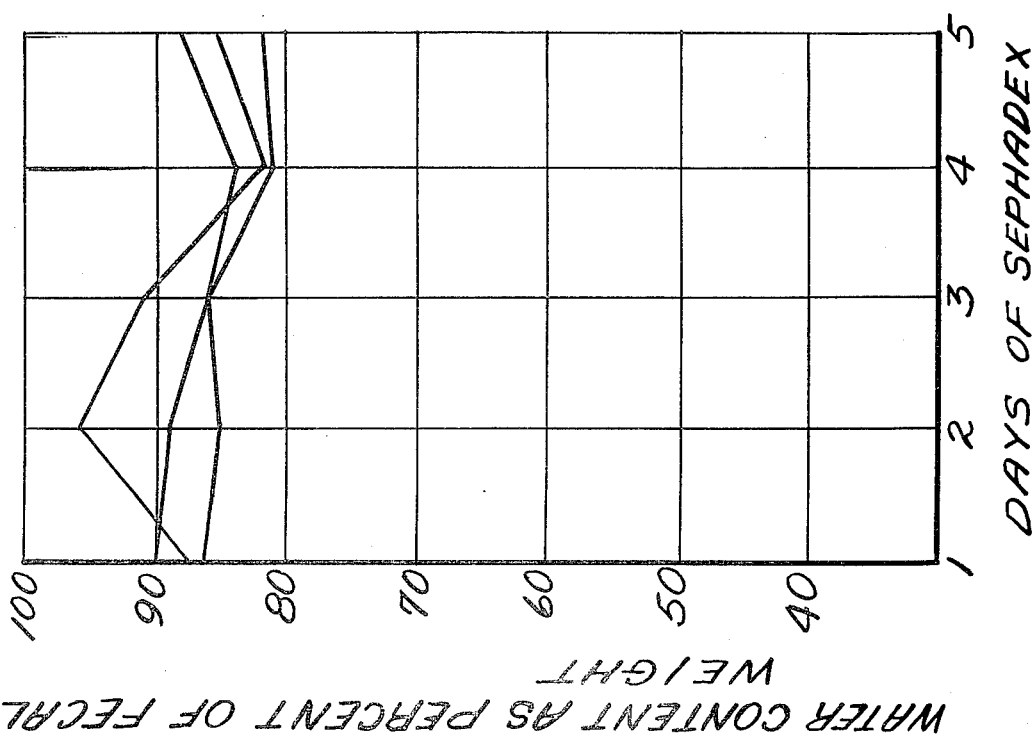

FIGS. 7A and 7B illustrate the results of an experiment demonstrating the effects of varying the amount of preferred insoluble, hydrophilic, cross-linked dextrans in the diets of rats. A group of 2 rats were given a diet which consisted of 10% by weight Sephadex G-100 and 90% by weight normal rat chow. Another group of 2 rats were given a diet which consisted of 25% by weight Sephadex G-100 and 75% by weight normal rat chow. A third group of 2 rats were given a diet consisting of 50% by weight Sephadex G-100 and 50% by weight normal rat chow. Each group was given this diet for a period of 5 consecutive days, and then each group was transferred to a normal diet consisting entirely of rat chow. After a period of four days of a normal diet, each group was again tested. FIG. 7A illustrates the results of the varying diets on the daily volume of urine of each group. It will be noted that in every case, the volume of urine of rats consuming a diet including an insoluble, hydrophilic, cross-linked dextran according to the present invention is substantially less than the volume of urine of the same group on a normal diet. It will further be observed that in every case, as the concentration of an insoluble, hydrophilic, cross-linked dextran is increased, the volume of urine in the treated group decreases. That is, the average daily volume of urine of rats given a diet including 25% by weight Sephadex G-100 is significantly less than the daily volume of urine of rats given a diet containing only 10% by weight Sephadex G-100. Similarly, the daily volume of urine of rats given a diet consisting of 50% by weight Sephadex G-100 is significantly less than the daily volume of urine of rats given a diet containing only 25% by weight Sephadex G-100. Thus, it may be seen that although amounts as little as 10% by weight of an insoluble, hydrophilic, cross-linked dextran according to the present invention is effective in substantially reducing the daily volume of urine, concentrations as high as 50% by weight of the total diet are preferred. FIG. 7B illustrates the water content of the feces of each of these groups of rats, again compared to the water content of the feces of the same rats fed a normal diet. In every case, it will be noted that the effect of treatment with an insoluble, hydrophilic, cross-linked dextran according to the present invention was to increase the water content of the feces of rats so treated, compared to rats consuming a normal diet. In every case, each rat was permitted to consume as much water as desired. The actual water consumed by each group of rats is listed in the table below:

| DAILY VOLUME OF WATER CONSUMED (IN MILLILITERS) | | | |
| --- | --- | --- | --- |
| Day | 10% G-100 | 25% G-100 | 50% G-100 |
| Sephadex-Containing Diet | | | |
| 1 | 68 | 103 | 73 |
| 2 | 56 | 81 | 73 |
| 3 | 69 | 69 | 73 |
| 4 | 61 | 74 | 78 |
| 5 | 55 | 78 | 67 |
| Normal Diet | | | |
| 1 | 45 | 52 | 45 |
| 2 | 53 | 46 | 55 |
| 3 | 45 | 42 | 54 |

These experiments show that diets containing insoluble, hydrophilic, cross-linked carbohydrates according to the present invention are able to divert water elimination from the renal route to the gastrointestinal route, and remove water from the body by the gastrointestinal route. These pharmalogical properties are of significant therapeutic value in the treatment of edema, water intoxication in chronic renal failure, and in the treatment of other forms of fluid retention such as congestive heart failure, cirrhosis of the liver and other disorders associated with refractory swelling. These pharmalogical properties are also useful as a means of reducing caloric intake, in the treatment of conditions such as obesity. Although the above experiments were conducted with animals other than human beings, preliminary experiments indicate that the insoluble, hydrophilic, cross-linked carbohydrates according to the present invention exhibit the same pharmalogical properties when used to treat human beings as in the treatment of other animals.

The present invention has been elucidated by the examples described above, but the invention is not limited thereto. It is understood that various other modifications will be apparent to and can readily be made by those skilled in the art without departing from the scope and spirit of this invention. Accordingly, it is not intended that the scope of the claims appended hereto be limited to the description set forth herein, but rather that the claims be construed as encompassing all the features of the present invention including all features which would be treated as equivalents thereof by those skilled in the art to which this invention pertains.

What is claimed is:

1. A method of treating edema in a host in need of such treatment because of renal failure which comprises orally administering to said host an effective amount of a water-insoluble hydrophilic, cross-linked polysaccharide which is capable of absorbing water in the lumen of the gastrointestinal tract and discharging the thus bound water by passage from the alimentary canal in the normal way.

2. A method according to claim 1 wherein said polysaccharide consists essentially of a copolymerization product in a gel grain form comprising a 3-dimensional macroscopic carbohydrate network, obtained from a neutral carbohydrate selected from the group consisting of dextran, sorbitol, starch, hydroxyethyl cellulose, dextrin, and sucrose and a bifunctional organic substance selected from the group consisting of epichlorohydrin, dichlorohydrin, diepoxybutane, bisepoxypropyl ether, ethylene glycol-bis-epoxypropyl ether, and 1,4-butan-diol-bis-epoxypropyl ether, bonded together by ether bridges of the general type —O—X—O— wherein X representa an aliphatic radical containing from 3 to 10 carbon atoms, the said copolymerization product being water-insoluble but being capable of absorbing water with swelling.

3. A method according to claim 1 wherein said polysaccharide is a copolymerization product in gel grain form comprising a 3-dimensional macroscopic network of dextran substances, built-up of chains of mainly alpha-1,6-glucosidically bonded glucose residues, bonded together by ether bridges of the general type —R—O—X—O—R—, wherein R represents the dextram substances and X is an aliphatic radical containing from 3 to 10 carbon atoms, the said copolymerization product being water-insoluble but being capable of absorbing water with swelling.

4. A method for treating obesity which comprises administering orally to a host in need of such treatment an effective amount of a water-insoluble hydrophilic, cross-linked polysaccharide which is capable of absorbing water with swelling in the lumen of the gastrointestinal tract, said oral administration being effective to eliminate the bound water via the gastro-intestinal route rather than by the renal route.

5. A method for treating edema in a mammal in need of such treatment which comprises administering orally to said mammal an effective amount of a water-insoluble hydrophilic, cross-linked polysaccharide which is capable of absorbing water with swelling.

6. A method for treating obesity in a mammal in need of such treatment which comprises administering orally to said mammal an effective amount of a water-insoluble hydrophilic, cross-linked polysaccharide which is capable of absorbing water with swelling.

7. A method for reducing the frequency of dialysis to a mammal in need of such treatment because of renal failure which comprises orally administering to said mammal an effective amount of a water-insoluble hydrophilic, cross-linked polysaccharide which is capable of absorbing water with swelling, and eliminating the bound water through the gastrointestinal route.

* * * * *